United States Patent [19]

Koros et al.

[11] Patent Number: 5,795,291
[45] Date of Patent: Aug. 18, 1998

[54] CERVICAL RETRACTOR SYSTEM

[76] Inventors: Tibor Koros; Gabriel Koros, both of 610 Flinn Ave., Moorpark, Calif. 93021

[21] Appl. No.: 796,878

[22] Filed: Feb. 7, 1997

Related U.S. Application Data

[63] Continuation of Ser. No. 351,804, Dec. 8, 1994, abandoned, and a continuation-in-part of Ser. No. 30,862, Nov. 10, 1994, Pat. No. Des. 369,860, and a continuation-in-part of Ser. No. 31,744, Dec. 5, 1994.

[51] Int. Cl.$^6$ .................................................. A61B 17/02
[52] U.S. Cl. ........................... 600/232; 600/235; 600/231; 600/213
[58] Field of Search ............................. 600/201, 227, 600/231, 232, 233, 234, 235, 213

[56] References Cited

U.S. PATENT DOCUMENTS

| | | | |
|---|---|---|---|
| 3,467,079 | 9/1969 | James | 600/232 |
| 4,421,107 | 12/1983 | Estes et al. | 600/233 |
| 4,616,635 | 10/1986 | Caspar et al. | 600/217 |
| 4,747,394 | 5/1988 | Wantanabe | |
| 5,052,373 | 10/1991 | Michelson | 600/232 |

FOREIGN PATENT DOCUMENTS 1456108  2/1989  U.S.S.R. .................... 600/232

OTHER PUBLICATIONS

Zimmer Medical/Surgical Products (Catalog). Blade 3065—02, Blade 3065—04, p. D 11, 1983.

Primary Examiner—Jeffrey A. Smith
Attorney, Agent, or Firm—Richard D. Slehofer

[57] ABSTRACT

A combination of complementary surgical instruments including a pair of retractors positioned at right angles to and overlaying one another during surgery. Each retractor has a pair of hinged arms. A top retractor has a stepped tip at each end of one arm to avoid interference with the bottom retractor during surgery. Each retractor has a pair of vertical semicircular flared openings in an outer edge of a blade securement end of a respective arm for demountable attachment of a surgical blade. The combination is especially useful in cervical or neck surgery.

7 Claims, 9 Drawing Sheets

CERVICAL RETRACTOR SYSTEM

CROSS REFERENCE TO RELATED APPLICATIONS

This is a continuation of Ser. No. 08/351,804, filed Dec. 8, 1994 which is abandoned. This is also a continuation-in-part application of Ser. No. 29/030,862, filed Nov. 10, 1994, now U.S. Pat. No. Des. 369,860. The present application is also a continuation-in-part of Ser. No. 29/031,744, filed Dec. 5, 1994, and which is currently pending.

BACKGROUND OF THE INVENTION

1. Field of the Invention

The present invention pertains to the following areas of technology:

SURGERY—Medical and laboratory Equipment; hand-held or manipulated surgical instrument or tool for medical or laboratory use.

2. Description of the Prior Art

In the early 1950's an operation was pioneered by Ralph B. Cloward, M.D. for the removal of ruptured cervical disc lesions and osteophytes by an anterior surgical approach. A herniated disc is a rupture or herniation of the intervertebral disc, especially between lumbar vertebrae. This usually causes pain in the affected side. An osteophyte is a bony excrescence or out-growth, which is usually branched in shape. The anterior surgical approach means that a transverse incision is made on the patient's throat just to the right of the wind pipe. The level of the lesions is identified before the operation either by injecting methylene blue dye into the disc under X-ray control the day before surgery or by a portable X-ray taken in the operating room with the needle inserted into the disc. Endotracheal general anaesthesia is used in most cases. The patient is placed in the supine position with the neck extended over a special neck rest. It is soft but firm and X-ray's can be taken through it. The head is turned to the left and secured to the table with an adhesive band across the forehead.

The location of the transverse incision is determined by the level of the lesion. The C5–6 disc lies beneath the cricoid cartilage and the adjacent disc one centimeter above or below. The various neck muscles and nerves are cut so that the anterior of the spinal cord is eventually exposed. A small rectangular retractor is placed around the disc area so that the surgeon has room within which to work. The disc that has the lesions is removed with a rongeur and a scalpel. The main objective of the Cloward procedure is to make at least one drill hole between the adjoining vertebrae to a sufficient depth but yet to prevent it from damaging any of the nerves contained within the spinal cord. After the drill hole has been completed, a complimentary bone plug is removed from the patient's hip. The bone plug from the patient's hip is then positioned into the drill hole made in the pair of vertebrae. The hip bone plug will then fuse with the two vertebrae to create one vertebra that is fused together.

The guide used for the drill hole is usually placed slightly off center to the right of the midline regardless of lateralization of lesion so the drill will remove more bone on the right side. The bottom of the drill guard has ins which have to be hammered into the surface of the vertebrae to secure the drill guard for the operation. The guard pins on the drill guard do not harm the spinal cord because of the neck rest under the neck. Three drill tip sizes are available in diameters of 11.5 mm, 13.5 mm, and 15.5 mm, to accommodate the variation and the size of the vertebral bodies and the width of the disc spaces. The drill tips are interchangeable on a single drill shaft and are adjustable in length with the guard. A relief opening in the drill guard permits escape of bone dust and prevents the drill from binding. When drilling is complete, the guard and drill are removed and the drill hole immediately fill with a gel foam pad soaked in topical thrombin and packed with a padding.

The dowel is attached to the impactor tip. If the bone graft is too long or too large it can be tailored with a file to the appropriate size. Some surgeons are apprehensive that the dowel may be driven into the spinal canal damaging the spinal cord. This is a serious but avoidable complication. It can be prevented by using a dowel impactor tip larger then the drill hole. This will permit the dowel to be inserted only flush with the vertebra. It must then be recessed slightly with the smaller impactor two millimeters below the outer rim of the drill hole. Heavy pounding is unnecessary and should not be done. The distance between the dura and the inner end of the dowel can be determined by lowering the osteophyte elevator into the interspace lateral to the drill hole. The foot of the elevator is placed beneath the dowel and raised gently up and down.

With the wound closure, all of the retractor blades are removed and the longus colli muscle is checked for bleeding points. Any bleeding from the outer margin of the drill hole or the guard pin holes can be arrested with bone wax.

Post operative pain from this operation is minimal and is controlled with mild analgesics. The patient is permitted to be up the day of the operation. Movements of neck are not restricted and no neck brace cast is required. A soft cervical collar is used for multiple level cases.

The patient is usually discharged from the hospital on the third or fourth day. X-rays are taken prior to discharge to determine the position of the bone graft or grafts and for comparison with subsequent follow-up films.

The parts which comprise the Cloward kit include: the skin retractor; cervical muscle retractor; blade retractor; cervical periosteal elevator; cervical retractor (large) with set of seven sharp blades; double hinged retractor handle; cervical retractor with seven blunt blades; rongeur; cervical vertebra spreader; depth gauge; the three drill tips of the three sizes previously mentioned; drill shaft with depth stop and drill guard; guard guide; drill guard cap; cervical hammer; cross bar handle; bone punch; tissue retractor; dowel cutter shaft; dowel cutter center pin; dowel holder; dowel handle and impactor set; and a curved cervical osteotome 4 mm in size.

SUMMARY AND OPERATION OF THE INVENTION

Figure 1:
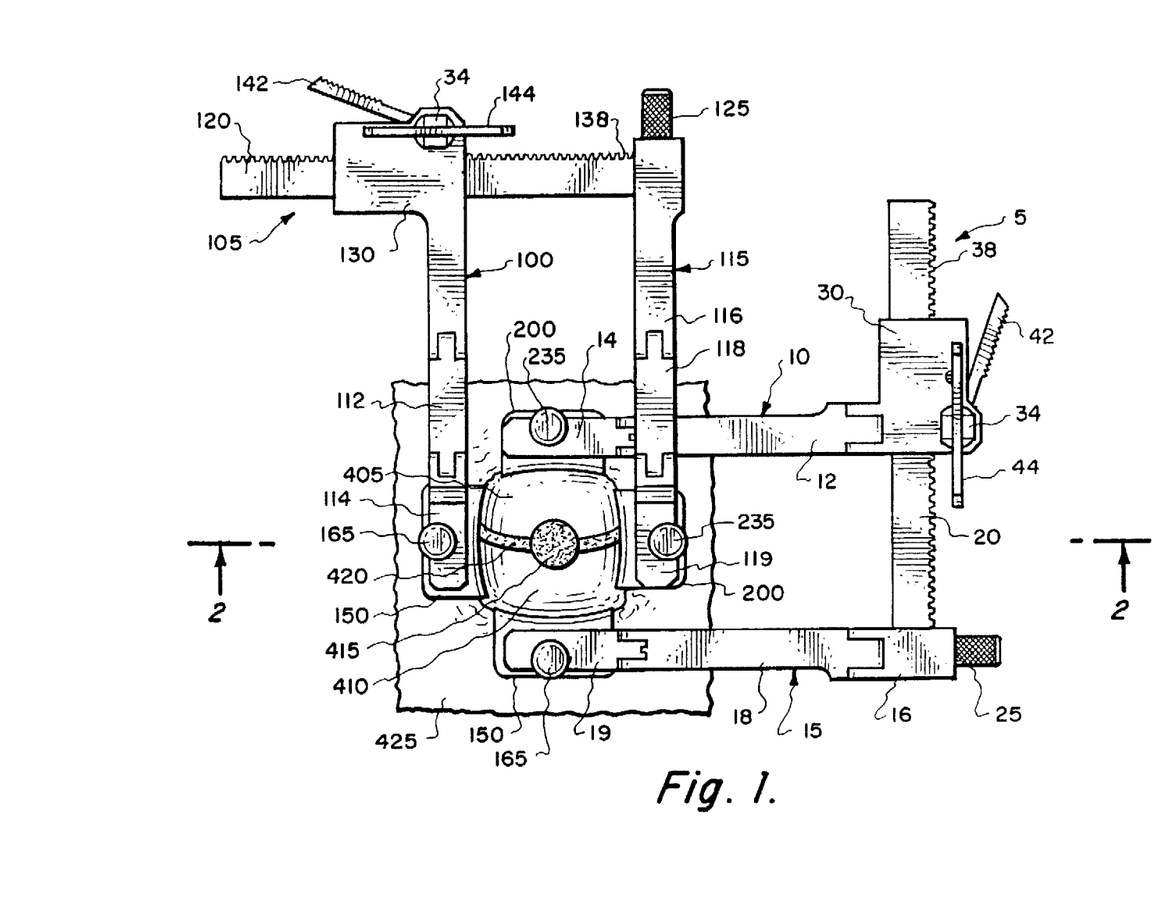
FIG. 1 is a top plan view of the present invention illustrating the offset retractor frame and the right retractor frame superposed over one another and being used in a cervical spine operation to implant a spinal implant between adjacent vertebrae in the neck area of the patient.
Figure 2:
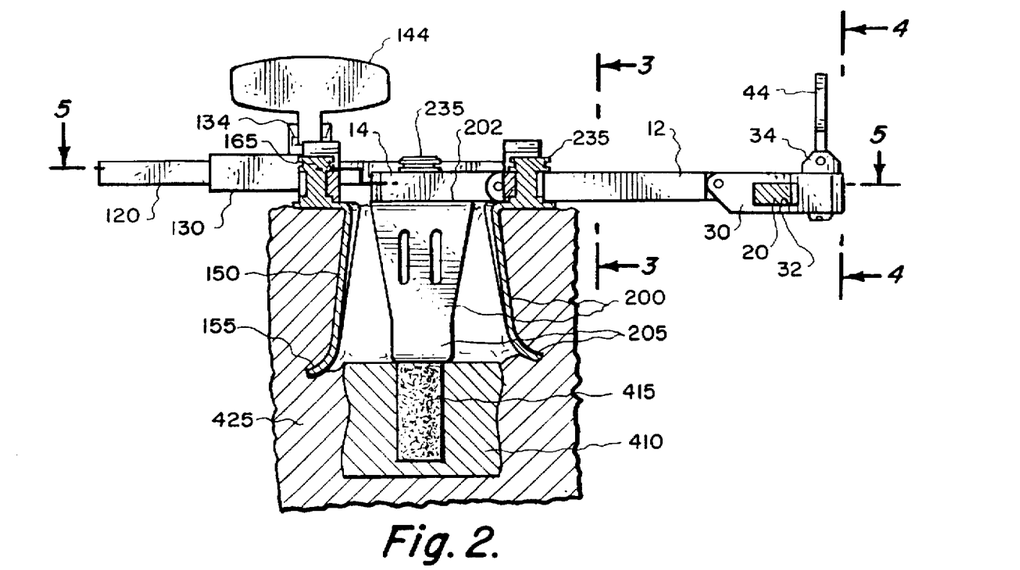
FIG. 2 is a vertical transverse sectional view taken along the line 2—2 of FIG. 1 and illustrating a spinal implant being surgically implanted in the cervical portion of the spine in a patient using the present invention.
Figure 3:
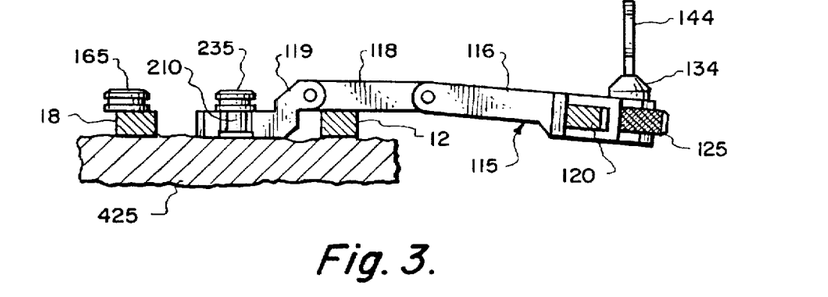
FIG. 3 is a vertical longitudinal sectional view taken along the line 3—3 in FIG. 2.
Figure 4:
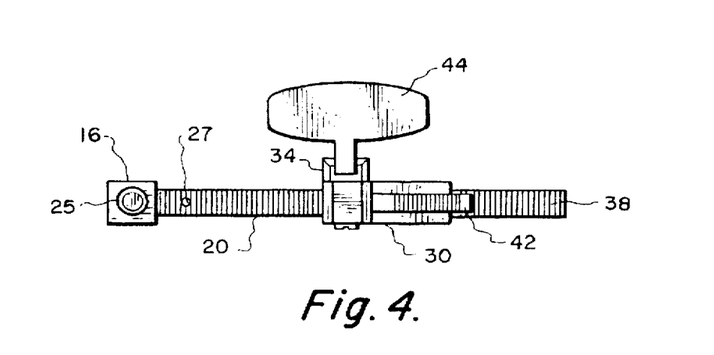
FIG. 4 is a vertical sectional view taken along the line 4—4 in FIG. 2.

The present invention is a collection of complementary surgical instruments used in neck surgery to remove a herniated disc from a pair of adjacent vertebrae or to fuse a pair of adjacent vertebrae with a spinal implant or both. It can also be used for spinal plieting. Cervical or neck surgery can be performed on the left or right anterior portion or the posterior portion of the patient's neck. The present invention includes a pair of compact lightweight retractors that are positioned at right angles to and overlay one another during the surgery. In larger operations three retractors should be used. Each retractor has a pair of hinged arms so that the invention will lie flat on the patient's neck. The top retractor has a stepped tip at each end of the arm to avoid interference with the bottom retractor during surgery. The tips of each arm on both retractors have semicircular indentations for mounting a blade in the indentation. The pair of universal retractors is arranged above the surgical incision so that four blades attached to the four retractor tips form a square box-like opening above the vertebra to give the surgeon clearance to perform the surgery. Six blades are used with three retractors in large operations. FIG. 1 shows the present invention properly in position while being used in a cervical spine operation to fuse a pair of adjacent vertebrae with a spinal implant. One, two, or three level fusion can be performed using the present invention. FIG. 2 illustrates three of the blades properly positioned in the patient's neck.

Each of the four surgical blades has a flat top and a curved vertical face. The bottom of the blades can have a plurality of curved tines or a solid curved edge. The vertical faces and the bottoms of the blades are important in retaining and holding back the soft tissue during the surgery. This also prevents the retractor frames from moving together during the surgery.

The flat top of each of the blades has a centrally mounted post with a knob mounted on the top of the post. A permanent circular washer surrounds the base of the post where the post is secured to the top of the blade. The dimensions of the post allow it to snugly fit in the indentation or semicircular flared opening at each tip of the retractor arms. The bottom of the knob on the blade engages the top of the retractor arm and the circular washer engages the bottom of arm. The post and knob slide into the indentation on the retractor tip. The blade can swivel about the axis of the post but does not move in any other direction. Each blade can be easily removed from the retractor. The soft tissues that are pried apart by the retractors and blades have a natural and strong tendency to return to their normal position. The tension of the soft tissues pressing against the vertical face of each blade prevents the post with the blade from dislodging from the retractor arm. The indentations are located on the outer edges of the blade securement end of each retractor arm.

Each blade is aligned, positioned into place at the site of the incision, and slid into place on the retractor arm with the assistance of a blade handle, which is illustrated in FIGS. 7-12. The blade handle has a screw activated lock at its base which clamps and securely locks the blade to the knob on the top of the blade. The handle with the locked blade extending from it is manipulated as a single unit. The post can still be slid into the key hole-shaped indentation. An assistant holds two handles with the attached blade in each hand and spreads apart the incision. A first or right retractor frame is then placed over the exposed soft tissue, and the retractor is cranked open until the blades are secured to the retractor arms. The retractor is then cranked open to it maximum opening while the handles are still attached to the blades. The surgeon then places a second or offset retractor frame at a right angle on top of the first retractor frame. An assistant then grasps a third handle with the attached blade and holds it in the incision area. Another assistant grasps a fourth handle with the attached blade and holds it in the incision area while the surgeon cranks open the second retractor frame. The third and fourth blades are then slid into position on the retractor arms and the retractor frame is cranked to its maximum desired opening by rotating the crank handle. The crank handle is hingedly attached to the crank pinion so that the handle can be folded flat and out of the way when not in use. Afterwards the four handles are unlocked from the blade knobs and removed to also be out of the way during the surgery. The present invention keeps a low profile during surgery to allow the surgeon an unobstructed surgical environment. After the spinal surgery is completed, each retractor frame is closed by depressing the crank release lever. The retractor frames and blades are removed, and the incision is closed.

DETAILED DESCRIPTION OF THE PREFERRED EMBODIMENT

The present invention will now be discussed in greater detail. FIG. 1 shows the present invention properly in position while being used in a cervical spine operation to fuse a pair of adjacent vertebrae 405 and 410 with a spinal implant 415. The disc 420 is located between the two vertebrae 405 and 410. The patient's soft tissue and muscles are collectively labelled 425. The right orientation retractor frame is labelled 5 and the offset retractor frame is labelled 105. A mirror image of the right orientation retractor could be fabricated and then referred to as a left orientation retractor frame. The choice of left or right retractor frame is determined by the site of the surgical incision. Additionally, combinations of the retractor frames could be used for three or more vertebrae fusions or discectomies performed during one operation. When three retractors are needed, a right retractor, a left retractor, and an offset retractor are used.

Figure 5:
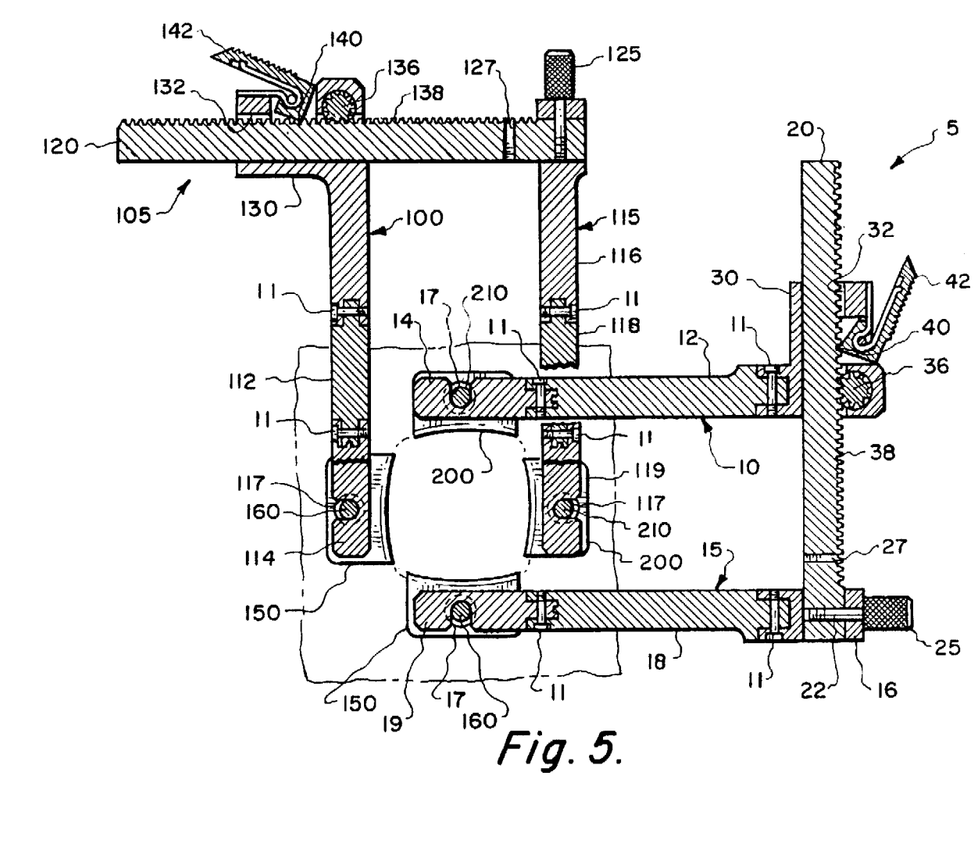
FIG. 5 is a transverse sectional view taken along the line 5—5 in FIG. 2.
Figure 6:
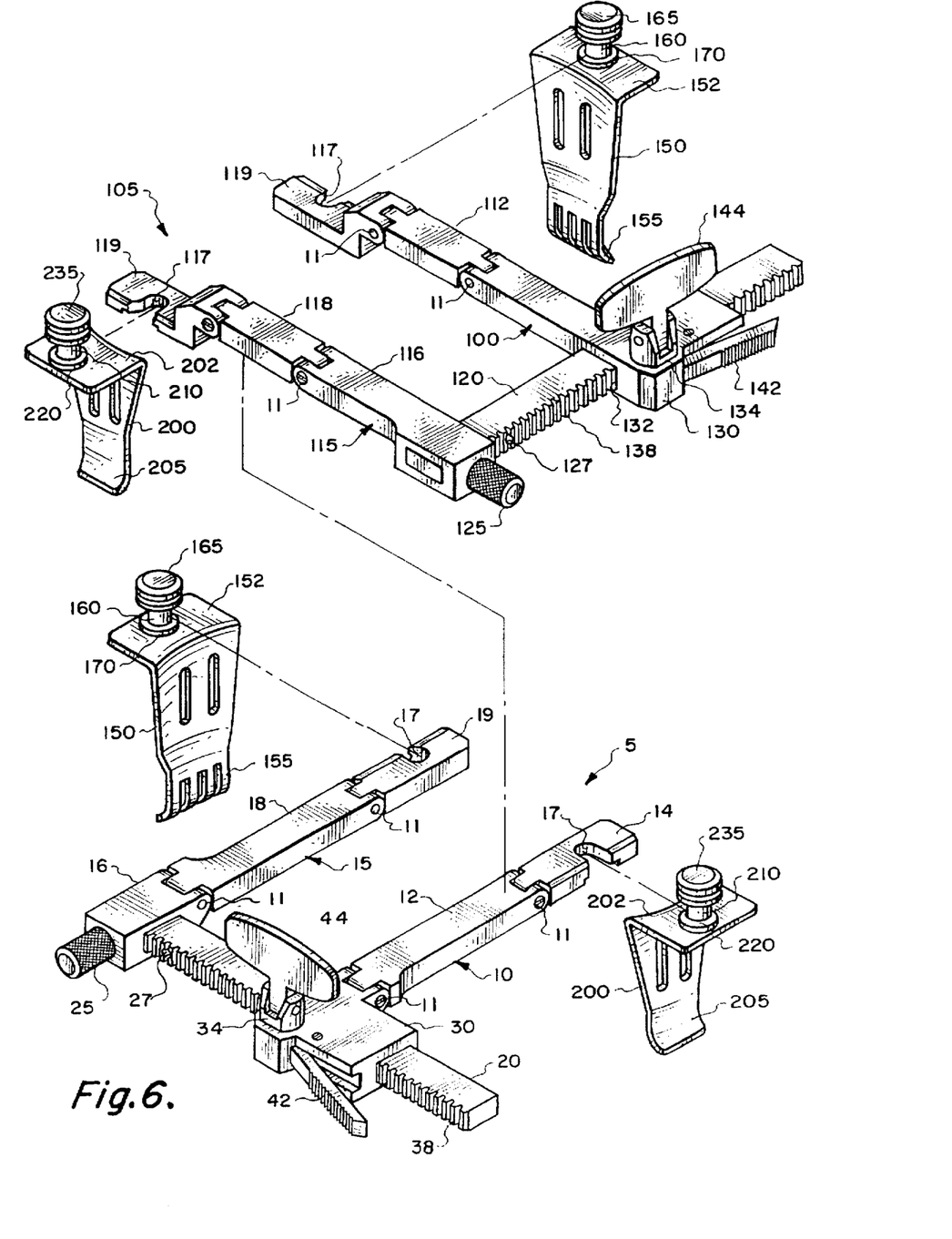
FIG. 6 is an exploded perspective view of the offset retractor frame, the right retractor frame, and four cervical microdiscectomy retractor blades.
Figure 7:
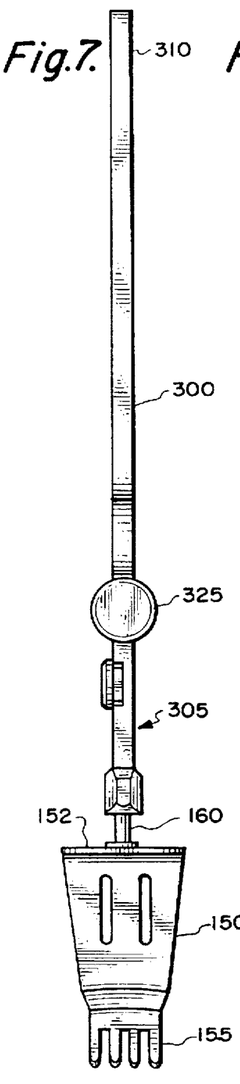
FIG. 7 is a front elevational view of a cervical and microdiscectomy retractor blade with a detachable handle.
Figures 8, 9, 10:
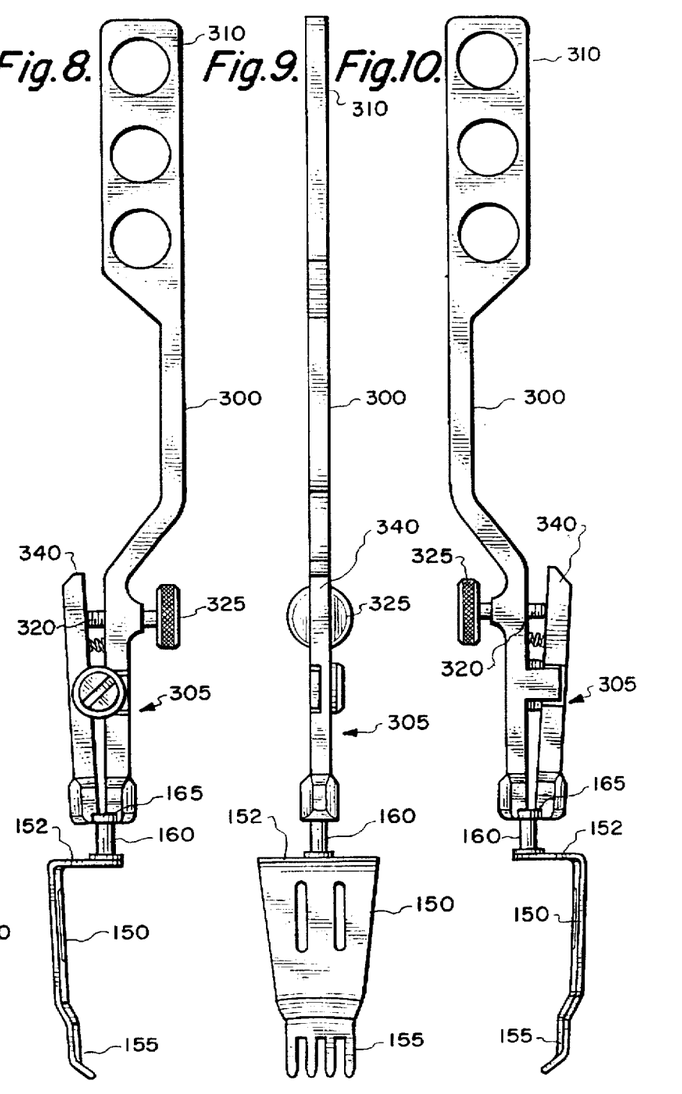
FIG. 8 is a right side elevational view of the blade and handle shown in FIG. 7.
FIG. 9 is a rear elevational view of the blade and handle shown in FIG. 7.
FIG. 10 is a left side elevational view of the blade and handle shown in FIG. 7.
Figure 11:
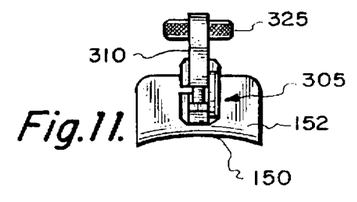
FIG. 11 is a top plan view of the blade and handle shown in FIG. 7.
Figure 12:
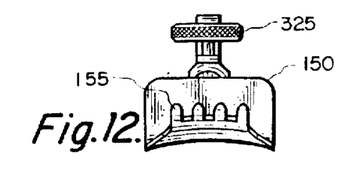
FIG. 12 is a bottom plan view of the blade and handle shown in FIG. 7.
Figure 13:
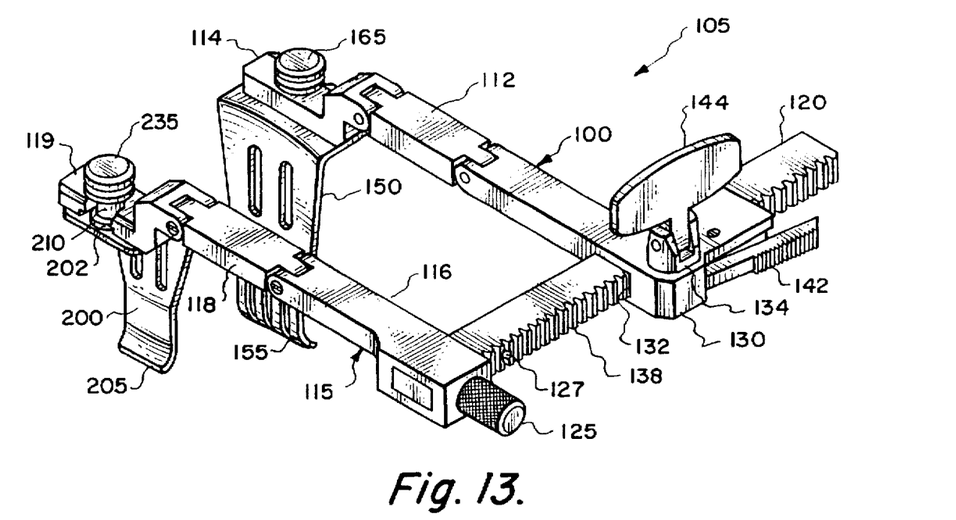
FIG. 13 is an isometric view of the offset retractor frame.
Figure 14:
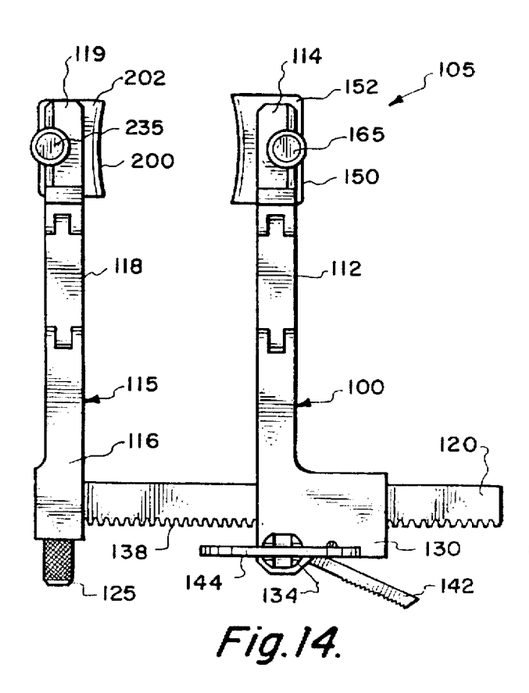
FIG. 14 is the front view of the offset retractor frame illustrated in FIG. 13.
Figure 15:
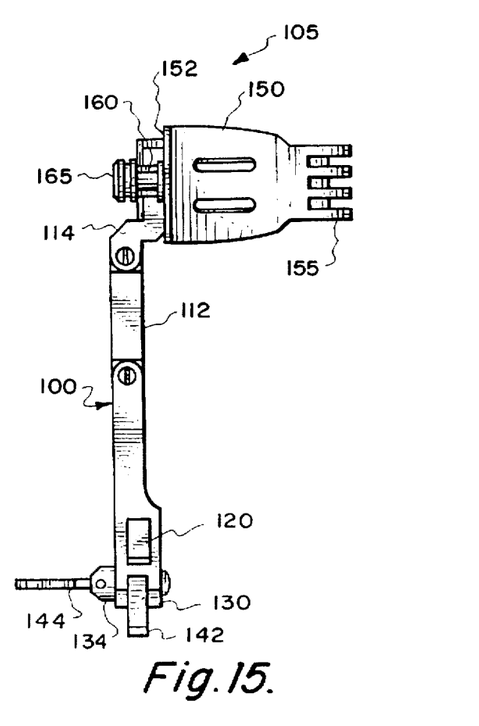
FIG. 15 is a right side view of the offset retractor frame illustrated in FIG. 13.
Figures 16, 17:
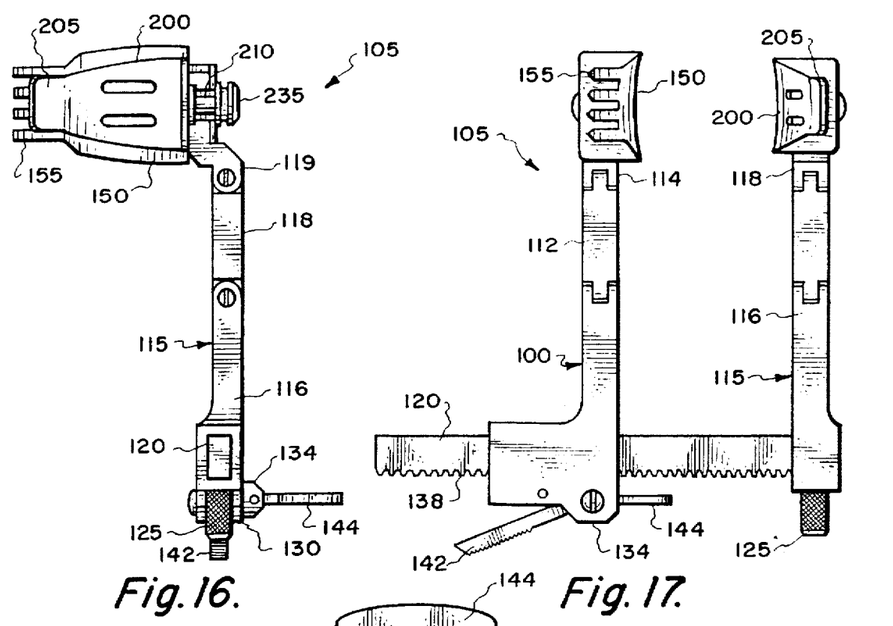
FIG. 16 is a left side view of the offset retractor frame illustrated in FIG. 13.
FIG. 17 is a rear view of the offset retractor frame illustrated in FIG. 13.
Figure 18:
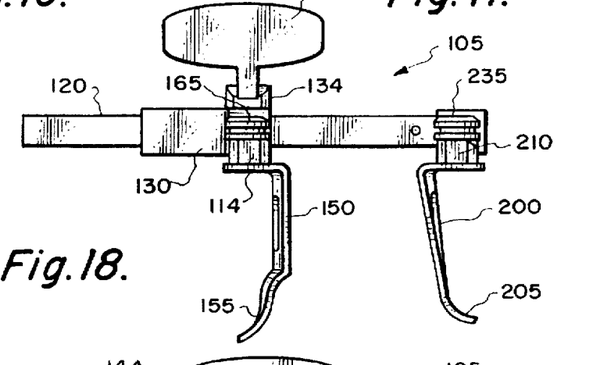
FIG. 18 is a top view of the offset retractor frame illustrated in FIG. 13.
Figure 19:
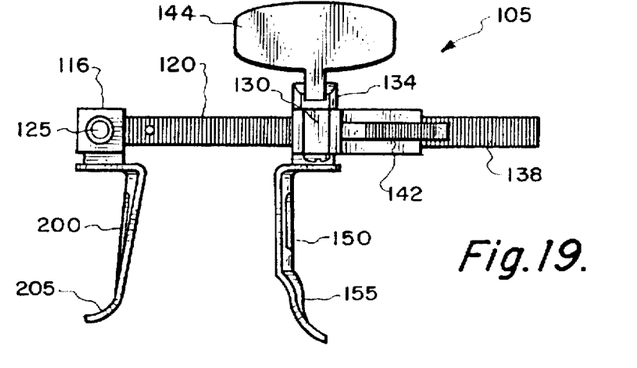
FIG. 19 is a bottom view of the offset retractor frame illustrated in FIG. 13.
Figure 20:
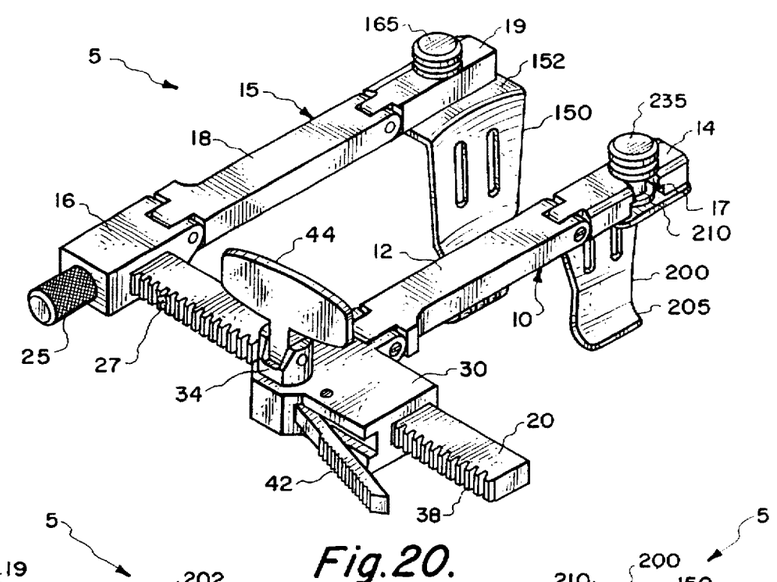
FIG. 20 is an isometric view of the right oriented retractor frame.
Figure 21:
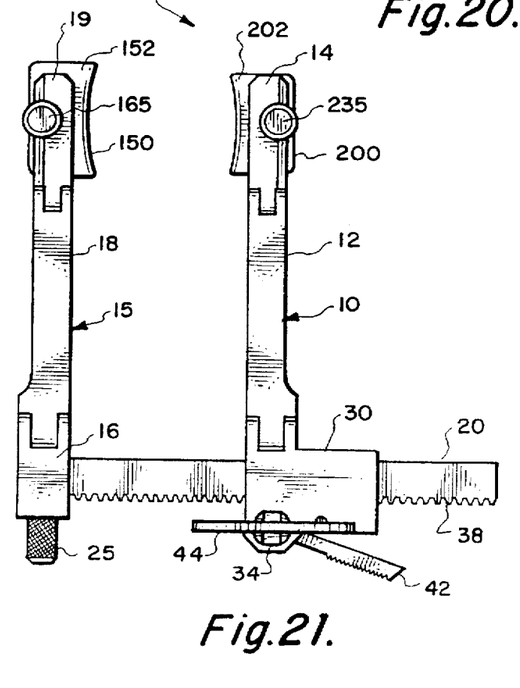
FIG. 21 is the front view of the right oriented retractor frame illustrated in FIG. 20.
Figure 22:
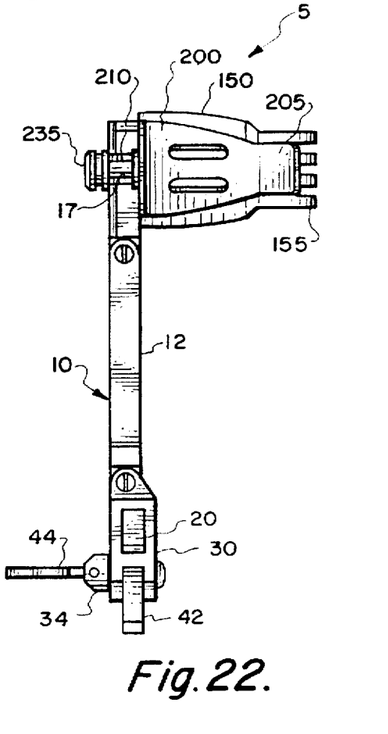
FIG. 22 is a right side view of the right oriented retractor frame illustrated in FIG. 20.
Figures 23, 24:
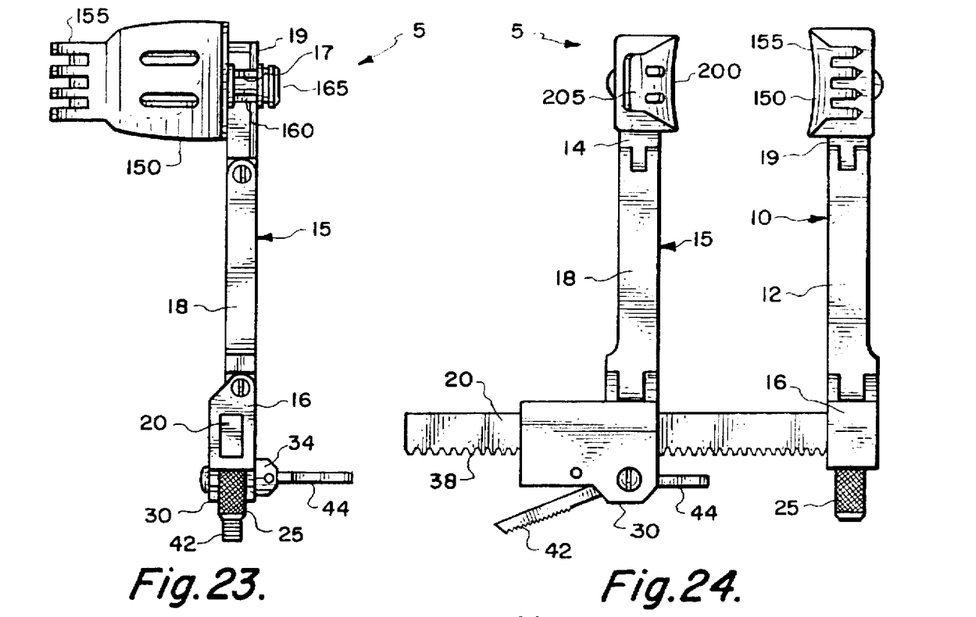
FIG. 23 is a left side view of the right oriented retractor frame illustrated in FIG. 20.
FIG. 24 is a rear view of the right oriented retractor frame illustrated in FIG. 20.
Figure 25:
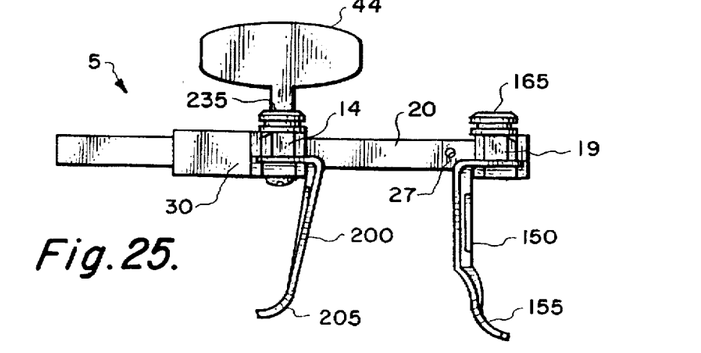
FIG. 25 is a top view of the right oriented retractor frame illustrated in FIG. 20.
Figure 26:
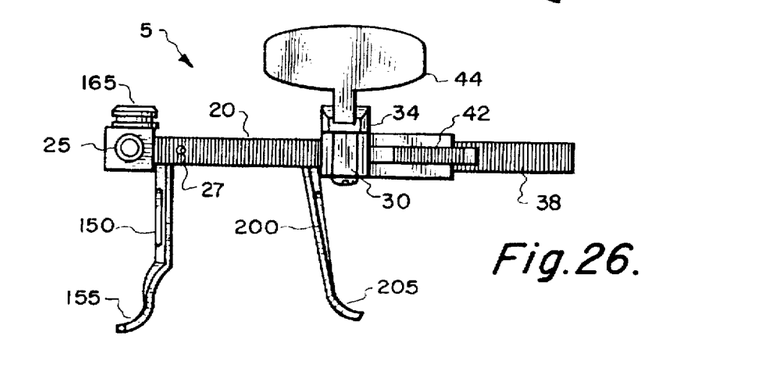
FIG. 26 is a bottom view of the right oriented retractor frame illustrated in FIG. 20.

The right retractor frame 5 includes a movable arm 10, a stationary arm 15, and a toothed cross brace or rack 20. One end of the toothed cross brace 20 is secured to the attachment end of the stationary arm 15 by means of a threaded screw 22 (FIG. 5) with a large knurled head 25 for ease in tightening and loosening the threaded screw 22. The rack 20 has at least one additional threaded hole 27 to allow the stationary arm 15 to be moved and fastened one-half inch inboard from the flush end fastening position. This allows the surgeon more flexibility when setting up the retractor frames for a particular operation. The stationary arm 15 can be separated from the rack by unscrewing the screw 22 and pulling the end of the rack from the stationary arm.

One end of the movable arm 10 has a housing 30 for slidably engaging the toothed cross bar or rack 20. The housing 30 has a slotted opening 32 running therethrough for receiving and slidably engaging a portion of the toothed cross bar or rack 20 therein. The housing 30 includes a crank 34 with a pinion gear 36 for engaging the toothed portion 38 of the toothed cross bar 20. The engagement between the teeth 38 on the cross bar and the pinion gear 36 on the crank 34 can be described as a rack and pinion combination. A pawl 40 with a quick release trigger 42 is included in the housing 30 of the movable arm 10. By rotating the crank handle 44, the movable arm 10 moves away from the stationary arm 15 and increases the gap between the pair of arms. The crank mechanism 34 is designed to turn in one direction to move the arm in one direction tooth by tooth away from the stationary arm. The movable arm 10 can be released from its cranked position by depressing the release trigger 42 to allow the movable arm 10 to slide back and forth along the toothed cross bar 20 without having to turn the crank 34 in the housing 30 of the movable arm 10.

The movable arm 10 and the stationary arm 15 are comprised of hinged segments to provide either arm with the ability to lie over an area that is not flat such as the patient's neck area. The movable arm 10 has a middle hinged segment 12, and a hinged end 14 or tip segment. The stationary arm 15 includes the stationary segment 16, the middle hinged segment 18 and the hinged end or tip segment 19. All of the hinged segments are held together with hinge screws 11. The contour of the area to be operated on can be accommodated with the hinged stationary arm 15 and movable arm 10. The stationary arm 15 and the movable arm 10 each comprise three hinged sections, as previously stated. Each arm is designed so that each one is stiff and rigid when force is applied horizontally, and yet each will move and flex vertically.

The outer edge of each movable arm 10 and stationary retractor arm 15 includes at least one cutaway receiving area 17 which can be described as a semicircular flared opening used as a temporary swivel securement point for one of the detachable surgical spreading and holding blades during the operation. Examples of different variants of the detachable blades are illustrated in FIGS. 1, 2, and 5–26.

The offset retractor frame 105 includes a movable arm 100, a stationary arm 115, and a toothed cross brace or rack 120. One end of the toothed cross brace 120 is secured to the attachment end of the stationary arm 115 by means of a threaded screw 122 with a large knurled head 125 for ease in tightening and loosening the threaded screw 122. The rack 120 has at least one additional threaded hole 127 to allow the stationary arm 115 to be moved and fastened one-half inch inboard from the flush end fastening position. This allows the surgeon more flexibility when setting up the retractor frame for a particular operation. The stationary arm 115 can be separated from the rack by unscrewing the screw 122 and then pulling the end of the rack from the stationary arm.

One end of the movable arm 100 has a housing 130 for slidably engaging the toothed cross bar or rack 120. The housing 130 has a slotted opening 132 running therethrough for receiving and slidably engaging a portion of the toothed cross bar or rack 120 therein. The housing 130 includes a crank 134 with a pinion gear 136 for engaging toothed portion 138 of the toothed cross bar 120. The engagement between the teeth 138 on the cross bar and the pinion gear 136 on the crank 134 could be described as a rack and pinion combination. A pawl 140 with a quick release trigger 142 is included in the housing 130 of the movable arm 100. By rotating the crank handle 144, the movable arm 100 moves away from the stationary arm 115 and increases the gap between the pair of arms. The crank mechanism 134 is designed to turn in one direction to move the arm 100 in one direction tooth by tooth away from the stationary arm 115. The movable arm 100 can be released from its cranked position by depressing the release trigger 142 to allow the movable arm 100 to slide back and forth along the toothed cross bar 120 without having to turn the crank 134 in the housing 130 of the movable arm 100.

The movable arm 100 and the stationary arm 115 are comprised of hinged segments to provide either arm with the ability to lie over an area that is not flat such as the patient's neck area. The movable arm 100 has a middle hinged segment 112 and a hinged end 114 or tip segment. The tip is stepped. The stationary arm 115 includes the stationary segment 116, the middle hinged segment 118 and the hinged end or tip segment 119. Tip 114 and tip 119 are mirror images of one another. The stepped configuration is clearly illustrated in FIG. 6. All of the hinged segments are held together with hinge screws 11. The contour of the area to be operated on can be accommodated with the hinged stationary arm 115 and movable arm 100. The stationary arm 115 and the movable arm 100 each comprise three hinged sections, as previously stated. Each arm is designed so that each one is stiff and rigid when force is applied horizontally, and yet each will move and flex vertically.

The outer edge of each movable arm 100 and stationary retractor arm 115 includes at least one cutaway receiving area 117 which can be described as a semicircular flared opening used as a temporary swivel securement point for one of the detachable surgical spreading and holding blades during the operation. Examples of different variants of the detachable blades are illustrated in FIGS. 1, 2, and 5–26.

Each of the four surgical blades used in the operation is actually comprised of two types of blades. Both types have a flat top and a concavo-convexo vertical face. The bottom of the blades can have a plurality of curved prongs 155 or a solid curved edge 205. The vertical faces and the bottoms of the blades are important in retaining and holding back the soft tissue during the surgery. The blade with the pronged bottom is labelled 150 and the blade with the solid bottom edge is labelled 200.

The flat top 152 of the pronged blade has a centrally mounted post 160 with a knob 165 mounted on the top of the post. A permanent circular washer 170 surrounds the base of the post where the post is secured to the top 152 of the blade. The dimensions of the post allow it to snugly fit in the indentation 17 and 117 at each tip of the retractors 5 and 105. The bottom of the knob 165 engages the top of the retractor arm tip 14, 17, 114 or 119, and the circular washer 170 engages the bottom of the arm tip. The post 160 and knob 165 slide into the indentation on the retractor tips.

The flat top 202 of the solid bottom edge blade 200 has a centrally mounted post 210 with a knob 235 mounted on the top of the post. A permanent circular washer 220 surrounds the base of the post where the post is secured to the top 202 of the blade. The dimensions of the post allow it to snugly fit in the indentations 17 and 117 at each tip of the retractors 5 and 105. The bottom of the knob 165 engages the top of the retractor arm tip 14, 17, 114 or 119, and the circular washer 220 engages the bottom of the arm tip. The post 210 and knob 235 slide into the indentation on the retractor tips. The semicircular identation also has a flat circular indentation for receiving the washer on the post.

Both blades 150 or 200 can swivel about the axis of the post but cannot move in any other direction. The blades can be easily removed from the retractor. The soft tissue that is pried apart by the retractors and blades have a natural and strong tendency to return to their normal position. The tension of the soft tissues pressing against the outer vertical faces of the blades prevents the post with the blade from dislodging from the retractor arm. This is clearly illustrated in FIG. 2. The indentations are located on the outer edges of the retractor arms.

Each blade is guided into place at the site of the incision with the assistance of a blade handle 300, and slid onto the retractor arm at the indentation. The blade handle is illustrated in FIGS. 7–12. The blade handle has a screw activated lock 305 at its base which clamps and securely locks and holds the knob 165 on the top of the blade 150. The upper part of the blade handle has a grip 310 for manually holding the blade handle 300. The grip 310 and base are one piece. A spring biased movable lock 340 is secured to the base of the handle. A threaded screw 320 with a large knurled head 325 is threadably inserted in the base portion and extends therethrough transversely so that the tip of the screw will force the movable lock 340 to close to clamp and hold the knob of a surgical blade.

The handle with the locked blade extending from it is manipulated as a single unit as illustrated in FIGS. 7–12. The post 165 can still be slid into the key hole-shaped indentation 17 or 117, because the clamp on the handle surrounds only the knob 165, and does not interfere with the post 160 or the retractor tips. An assistant holds two handles with the attached blade in each hand and spreads apart the incision. The right retractor is then placed over the exposed soft tissue, and the retractor is cranked open until the blades are secured to the retractor arms. The retractor is cranked open to it maximum opening while the handles are still attached to the blades. The surgeon then places the second offset retractor frame at a right angle on top of the first retractor frame. An assistant then grasps another pair of handles with attached blades and holds them in the incision area while the surgeon cranks open the second retractor frame. Both blades are then slid into position on the retractor arms and the retractor frame is cranked to its maximum desired opening by rotating the crank handle. The crank handle is hingedly attached to the crank pinion so that the handle can be folded flat and out of the way when not in use. Afterwards the four blade handles 300 are unlocked from the blade knobs and removed to also be out of the way during the surgery.

The present invention keeps a low profile during surgery to allow the surgeon room to work with. The offset retractor has lowered tips so that all four retractor tips are in the same plane with the surgical blades. After the spinal surgery is completed, each retractor frame is closed by depressing the crank release lever. The retractor frames and blades are removed, and the incision is closed.

Obviously, many modifications and variants of the present invention are possible in light of the above teachings. It is therefore to be understood that the full scope of the invention is not limited to the details disclosed herein, but may be practiced otherwise than as specifically described.

What is claimed is:

1. A right oriented cervical retractor comprising:

a stationary double hinged arm having a stationary segment, a middle hinged segment, and a hinged blade securement end having an outer edge;

a toothed cross brace having one end secured to said stationary segment of said stationary arm;

a movable double hinged arm having a housing for slidably engaging a portion of said toothed cross brace, a middle hinged segment, and a hinged blade securement end having an outer edge;

said housing on said movable hinged arm having a crank means for moving said movable arm away from said stationary arm;

a vertical semicircular flared opening in the outer edge of said blade securement end of said stationary arm for demountable attachment of a surgical blade; and a vertical semicircular flared opening in the outer edge of said blade securement end of said movable arm for demountable attachment of a surgical blade.

2. The retractor as recited in claim 1 including:

a surgical blade demountably secured to said vertical semicircular flared opening in the outer edge of said blade securement end of said stationary arm;

a surgical blade demountably secured to said vertical semicircular flared opening in the outer edge of said blade securement end of said movable arm;

each said blade having a generally flat top and a generally vertical face;

a vertical post with a knob mounted on said top of each said blade;

said post being positioned into said semicircular flared opening on each said stationary arm and said movable arm by a side loading movement to form a swivel lock to prevent disengagement of said blade from said arms during surgery because of the patient's soft tissue pressing against said vertical face of each said surgical blade.

3. The retractor as recited in claim 2 further comprising:

a blade handle for clamping over said knob on said blade for allowing said blade to be positioned in place and then secured to said arm during surgery.

4. An offset cervical retractor comprising:

a stationary double hinged arm having a stationary segment, a middle hinged segment, and an offset hinged blade securement end having an outer edge;

a toothed cross brace having one end secured to said stationary segment of said stationary arm;

a movable double hinged arm having a housing for slidably engaging a portion of said toothed cross brace, a middle hinged segment, and a hinged offset blade securement end having an outer edge;

said housing on said movable hinged arm having a crank means for moving said movable arm away from said stationary arm;

a vertical semicircular flared opening in the outer edge of said offset blade securement end of said stationary arm for demountable attachment of a surgical blade; and a vertical semicircular flared opening in the outer edge of said offset blade securement end of said movable arm for demountable attachment of a surgical blade.

5. The retractor as recited in claim 4 including:

a surgical blade demountably secured to said vertical semicircular flared opening in the outer edge of said blade securement end of said stationary arm;

a surgical blade demountably secured to said vertical semicircular flared opening in the outer edge of said blade securement end of said movable arm;

each said blade having a generally flat top and a generally vertical face;

a vertical post with a knob mounted on said top of each said blade;

said post being positioned into said semicircular flared opening on each said stationary arm and said movable arm by a side loading movement to form a swivel lock to prevent disengagement of said blade from said arms during surgery because of the patient's soft tissue pressing against said vertical face of each said surgical blade.

6. The retractor as recited in claim 4 further comprising:

a blade handle for clamping over said knob on said blade for allowing said blade to be positioned in place and then secured to said arm during surgery.

7. A right oriented cervical retractor and an offset cervical retractor in combination for use in cervical surgery comprising:

a right oriented cervical retractor comprising:

a stationary double hinged arm having a stationary segment, a middle hinged segment, and a hinged blade securement end having an outer edge;

a toothed cross brace having one end secured to said stationary segment of said stationary arm;

a movable double hinged arm having a housing for slidably engaging a portion of said toothed cross brace, a middle hinged segment, and a hinged blade securement end having an outer edge;

said housing on said movable hinged arm having a crank means for moving said movable arm away from said stationary arm;

a vertical semicircular flared opening in the outer edge of said blade securement end of said stationary arm for demountable attachment of a surgical blade;

a vertical semicircular flared opening in the outer edge of said blade securement end of said movable arm for demountable attachment of a surgical blade;

an offset cervical retractor overlying said right oriented cervical retractor and comprising:

a stationary double hinged arm having a stationary segment, a middle hinged segment, and an offset hinged blade securement end having an outer edge;

a toothed cross brace having one end secured to said stationary segment of said stationary arm;

a movable double hinged arm having a housing for slidably engaging a portion of said toothed cross brace, a middle hinged segment, and a hinged offset blade securement end having an outer edge;

said housing on said movable hinged arm having a crank means for moving said movable arm away from said stationary arm;

a vertical semicircular flared opening in the outer edge of said offset blade securement end of said stationary arm for demountable attachment of a surgical blade; and a vertical semicircular flared opening in the outer edge of said offset blade securement end of said movable arm for demountable attachment of a surgical blade.

* * * * *